(12) United States Patent
Zhang

(10) Patent No.: US 8,983,157 B2
(45) Date of Patent: Mar. 17, 2015

(54) SYSTEM AND METHOD FOR DETERMINING THE POSITION OF A HAIR TAIL ON A BODY SURFACE

(71) Applicant: Restoration Robotics, Inc., San Jose, CA (US)

(72) Inventor: Hui Zhang, San Jose, CA (US)

(73) Assignee: Restoration Robotics, Inc., San Jose, CA (US)

( * ) Notice: Subject to any disclaimer, the term of this patent is extended or adjusted under 35 U.S.C. 154(b) by 245 days.

(21) Appl. No.: 13/802,606

(22) Filed: Mar. 13, 2013

(65) Prior Publication Data

US 2014/0276958 A1    Sep. 18, 2014

(51) Int. Cl.
| | |
|---|---|
| *G06K 9/00* | (2006.01) |
| *G06K 9/66* | (2006.01) |
| *A61B 19/00* | (2006.01) |
| *G06T 7/00* | (2006.01) |

(52) U.S. Cl.
CPC ............. *A61B 19/5225* (2013.01); *G06T 7/004* (2013.01)
USPC .......................................... 382/128; 382/195

(58) Field of Classification Search
USPC .................................................. 382/128, 195
See application file for complete search history.

(56) References Cited

U.S. PATENT DOCUMENTS

| | | | |
|---|---|---|---|
| 6,141,431 A * | 10/2000 | Munetsugu et al. .......... 382/100 |
| 6,230,046 B1 | 5/2001 | Crane et al. | |
| 7,217,266 B2 | 5/2007 | Anderson et al. | |
| 7,477,782 B2 * | 1/2009 | Qureshi et al. ................ 382/171 |
| 7,627,157 B2 | 12/2009 | Qureshi et al. | |
| RE42,381 E | 5/2011 | Gildenberg | |
| 8,199,983 B2 * | 6/2012 | Qureshi et al. ................ 382/128 |
| 2003/0120298 A1 | 6/2003 | Gildenberg | |
| 2006/0089555 A1 * | 4/2006 | Gummer et al. ............. 600/476 |
| 2006/0127881 A1 | 6/2006 | Wong et al. | |
| 2007/0038118 A1 | 2/2007 | DePue et al. | |
| 2007/0106307 A1 * | 5/2007 | Bodduluri et al. ............ 606/133 |
| 2008/0033455 A1 | 2/2008 | Rassman et al. | |
| 2008/0242990 A1 | 10/2008 | Zanelli et al. | |
| 2009/0245601 A1 | 10/2009 | Cohen et al. | |
| 2009/0306498 A1 | 12/2009 | Bodduluri et al. | |
| 2010/0234871 A1 * | 9/2010 | Qureshi et al. ................ 606/187 |
| 2010/0262129 A1 * | 10/2010 | Roy et al. ........................ 606/10 |
| 2011/0082369 A1 | 4/2011 | Mohr et al. | |
| 2013/0061866 A1 * | 3/2013 | Klingelmeyer et al. ...... 132/208 |

FOREIGN PATENT DOCUMENTS

WO    WO 03/044737    5/2003

OTHER PUBLICATIONS

Bernstein, et al., "Follicular Transplantation", International Journal of Aesthetic and Restorative Surgery. Volume 3, No. 2., 1995, 119-132.

(Continued)

*Primary Examiner* — Uptal Shah
(74) *Attorney, Agent, or Firm* — Lena I. Vinitskaya; Sharon Upham

(57) ABSTRACT

System and method are provided for determining hair tail positions. An image containing hair which is received from an image acquisition device is processed to find a coarse hair tail position. The coarse hair tail position is refined through further processing. The refined hair tail position may be used for accurate positioning, for example, of hair transplantation tools in various hair transplantation applications.

29 Claims, 9 Drawing Sheets

(56) References Cited

OTHER PUBLICATIONS

Hoffman, et al., "Recent Findings with Computerized Methods for Scalp Hair Growth Measurements", The Journal of investigative dermatology symposium proceedings 2005, vol. 10, No. 3, 2005, pp. 285-288.

Jain, et al., "Machine Vision, Chapter 4+5, McGraw-Hill, Inc.", 1995.

Khan, et al., "Optical Clearing of In Vivo Human Skin: Implications for Light-Based Diagnostic Imaging and Therapeutics", Lasers in Surgery and Medicine 34,, 2004, pp. 83-85.

Laubscher, et al., "Video-Rate Three-Dimensional Optical Coherence Tomography", Optics Express. vol. 10, No. 9;, May 6, 2002., pp. 429-435.

Lyubovitsky, et al., "In Situ Multiphoton Optical Tomography of Hair Follicles in Mice", Journal of Biomedical Optics, 12(4), 044003 (Jul./Aug. 2007)., 2007, pp. 044003-8.

Pan, et al., "Noninvasive Imaging of Living Human Skin with Dual-Wavelength Optical Coherence Tomography in Two and Three Dimensions", Journal of Biomedical Optics 3(4)., Oct. 1998, pp. 446-455.

Welzel, "Optical Coherence Tomography in Dermatology: a Review", Skin Research and Technology, 2001; 7, 2001, pp. 1-9.

PCT International Search Report and Written Opinion mailed Jul. 15, 2014, in connection with commonly assigned International Application No. PCT/US2014/021980 (14 pages).

* cited by examiner

SYSTEM AND METHOD FOR DETERMINING THE POSITION OF A HAIR TAIL ON A BODY SURFACE

FIELD OF THE INVENTION

This invention relates generally to medical and cosmetic/aesthetic procedures, for example, hair transplantation procedures, and more particularly to a system and method for determining the position of hair tails on a body surface.

BACKGROUND

With reference, for example, to hair transplantation, manual and automatic hair transplantation procedures are known. For example, in a patient having male pattern baldness, hair transplantation typically involves harvesting donor hair grafts from the side and back fringe areas (donor areas) of the patient's scalp, and implanting them in a bald area (recipient area). In one known manual method, a linear portion of the scalp is removed from a donor area by dissection with a scalpel down into the fatty subcutaneous tissue. The strip is dissected (under a microscope) into the "follicular units," which are then implanted into a recipient area in respective holes or sites made by an implanting tool. Follicular units (also referred to herein as FU or FUs) are naturally occurring aggregates of 1-3 (and much less commonly, 4-5) closely spaced hair follicles that are distributed randomly over the surface of the scalp.

Some of the known automated systems and methods for transplanting hair are disclosed in U.S. Pat. No. 6,585,746 and U.S. Publication No. 2007/0106306, which are hereby incorporated by reference in their entirety. Generally, such automated systems comprise a robotic arm having a harvesting and/or implantation tool mounted on the arm. One or more cameras are also mounted on the arm and are used to image the body surface. A processor is configured to receive and process images acquired by the cameras. A controller is operatively coupled to the processor and the robotic arm. The controller controls the movement of the robotic arm based, at least in part, on the processed images acquired by the cameras and the processor. The arm is controllably moveable to position the tool at a desired orientation and position relative to the body surface to perform harvesting and transplanting hairs.

Hair transplantation requires selecting the follicular units to be harvested and removing them for implanting into a recipient area (e.g., bald area). The follicular units may be classified, or "typed," based on the number of hair follicles in the unit and identified in shorthand as an "F1" for a single hair follicular unit, an "F2" for a two hair follicular unit and so on for follicular units with 3-5 hairs. In some cases of follicular units comprising multiple hair follicles, the multiple hair follicles may appear to emerge from a single point in the skin. In other cases of follicular units comprising multiple hair follicles, the hair follicles may emerge from or exit the skin surface at slightly spaced apart positions.

Each hair follicle has the following end points. One end point, typically located on the surface of the skin, is called the "tail." Hair tail is the point from which hair follicle emerges from the skin. Another end point is called the "head" and corresponds to the tip of each hair of the follicular unit lying above the skin surface. Thus, a single-hair follicular unit has one head and one tail, while a two-hair follicular unit has two heads and two tails (although the tails of each hair follicle in some follicular units may emerge from the same point on the skin and appear as one tail only).

For harvesting, it is desirable to know exactly where hairs of the follicular unit emerge from the skin. For example in various automated or image-guided procedures, inaccurate hair tail position determination can adversely impact baseline information for reconstructing hair plane, or affect proper positioning of the tool used in the procedure relative to the hair, which may result in damaging hair graft (e.g. transecting hair follicle during harvesting).

Therefore, there is a need for a more efficient and accurate determination of hair tail position on a body surface.

SUMMARY OF THE INVENTION

Briefly, in accordance with one general aspect, the present application discloses systems and methods for improving accurate determination of a position of a hair tail on a body surface, including using obtained hair tail position information in performing various procedures, for example, hair harvesting or hair removal. According to one aspect of the present application, a method is provided for determining position of a hair tail on a body surface. The method comprises determining a contour of a hair from an image taken by an imaging device and determining a longitudinal or major axis of the hair. Also, intersecting points of the longitudinal axis and contour are determined, wherein one of the intersection points is associated with a coarse hair tail position on a body surface. An intensity profile along the longitudinal axis is generated and the coarse position of the hair tail is refined based on at least the intensity profile of the image. Any or all steps of the method may be implemented using a processor. Various image segmentation techniques may be used in various implementations to determine the contour of the hair follicles, for example, whether they be singular hair follicles or part of a follicular unit.

For follicular units comprising multiple or a plurality of hair follicles certain criteria may be defined to decide whether hair tail refinement should be applied to some or all of the plurality of hairs. Such criteria may be defined in terms of the distance, angle, position, e.g., co-location, of the multiple hairs relative to each other. Under one embodiment, when the follicular unit comprises a plurality of hairs, coarse positions of hair tails associated with each one of the plurality of hairs of the follicular unit may be refined. Alternatively, coarse position of a hair tail associated with at least one hair but not all of the plurality of hairs may be refined. In one example, when a plurality of hairs exits the body surface through a common point, coarse position of a hair tail associated with only one hair of such co-located hairs may be refined and such refinement may be applied to the rest of the plurality of hairs that exit the body surface through the common point. In another example, when two hairs exit the body surface at a distance that is less than a defined threshold distance from each other, coarse position of a hair tail associated with only one hair of such closely located hairs may be refined and the refinement is applied to the other hair. However, in some implementations, even if, for example, two hairs of the follicular unit exit the skin surface near the same point, the hair tails of both hairs may be refined. In still another example, two hairs that exit the body surface at an angle that is less than a defined angle, coarse position of a hair tail associated with only one hair may be refined and the refinement may be applied to the other one.

In some embodiments, the longitudinal axis and its corresponding orientation angle may be derived from the first order moment of the contour, with its position determined by the center of the region bound by the contour. In some embodiments, a plurality of orientation axes that are generally substantially parallel to the longitudinal axis are used for generating the intensity profile.

In some embodiments, statistical information associated with the hair image intensity profile, such as standard deviation, may be used for refining the hair tail position. In one embodiment, a refined intensity range derived from averaged intensities within a central region of the intensity profile plus a number of standard deviations is used for refining the hair tail position. For example, a refined intensity range may span two times the standard deviation on either side of the average intensity value. According to still other more detailed features of the present invention, refined positions of the hair tail derived from a plurality of images of a body surface are averaged. Alternatively, refined positions of the hair tail derived from a plurality of sequentially taken images of a body surface can be compared, for example, by smooth filtering.

According to another aspect of the present application, a method is provided for improving position of a hair harvesting tool relative to a hair graft to be harvested. The method comprising: determining a contour of a hair of a hair graft from an image of a body surface taken by an imaging device; determining a longitudinal axis of the hair; determining intersection points of said longitudinal axis of the hair and said contour of the hair, wherein one of the intersection points is associated with a coarse position of a hair tail of the hair on the body surface; generating an intensity profile of the image of the hair along the longitudinal axis of the hair; refining the coarse position of the hair tail based on at least the intensity profile of the image; and positioning a hair harvesting tool relative to the hair graft based on the refined position of the hair tail of the hair of the hair graft.

According to yet another aspect of the present application, a system for determining a position of a hair tail on a body surface is provided. The system may comprise a receiver configured to receive an image of a hair on a body surface and a processor configured to execute instructions for refining a coarse position of a hair tail of the hair, wherein the coarse position is refined based on at least an intensity profile of the image of the hair.

According to yet another aspect of the present application, a system is provided comprising an imaging device configured for capturing images and an image processor configured to process images captures by the imaging device. The image processor may comprise one or more modules for executing operations on the images, the one or more modules comprising: a hair segmentation module configured to segment the captured image; a detector module configured to determine a coarse position of a hair tail, and a hair refinement module configured to refine the coarse position of the hair tail.

According to a further aspect of the present application, an image processor is provided, the image processor comprising one or more modules for executing operations on images, the one or more modules comprising instructions for: determining a contour of a hair from an image of a body surface taken by an imaging device; determining a longitudinal axis of the hair; determining intersection points of the longitudinal axis of the hair and the contour of the hair, wherein one of the intersection points is associated with a coarse position of a hair tail of the hair on the body surface; generating an intensity profile of the image along the longitudinal axis of the hair; and refining the coarse position of the hair tail based on at least the intensity profile of the image.

BRIEF DESCRIPTION OF THE DRAWINGS

The present invention is described with reference to the accompanying drawings. It should be noted that the drawings are not to scale and are intended only as an aid in conjunction with the explanations in the following detailed description. In the drawings, identical reference numbers identify functionally similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Features and advantages of the present invention will become appreciated as the same become better understood with reference to the specification, claims, and appended drawings wherein:

DETAILED DESCRIPTION OF THE INVENTION

Figure 1A:
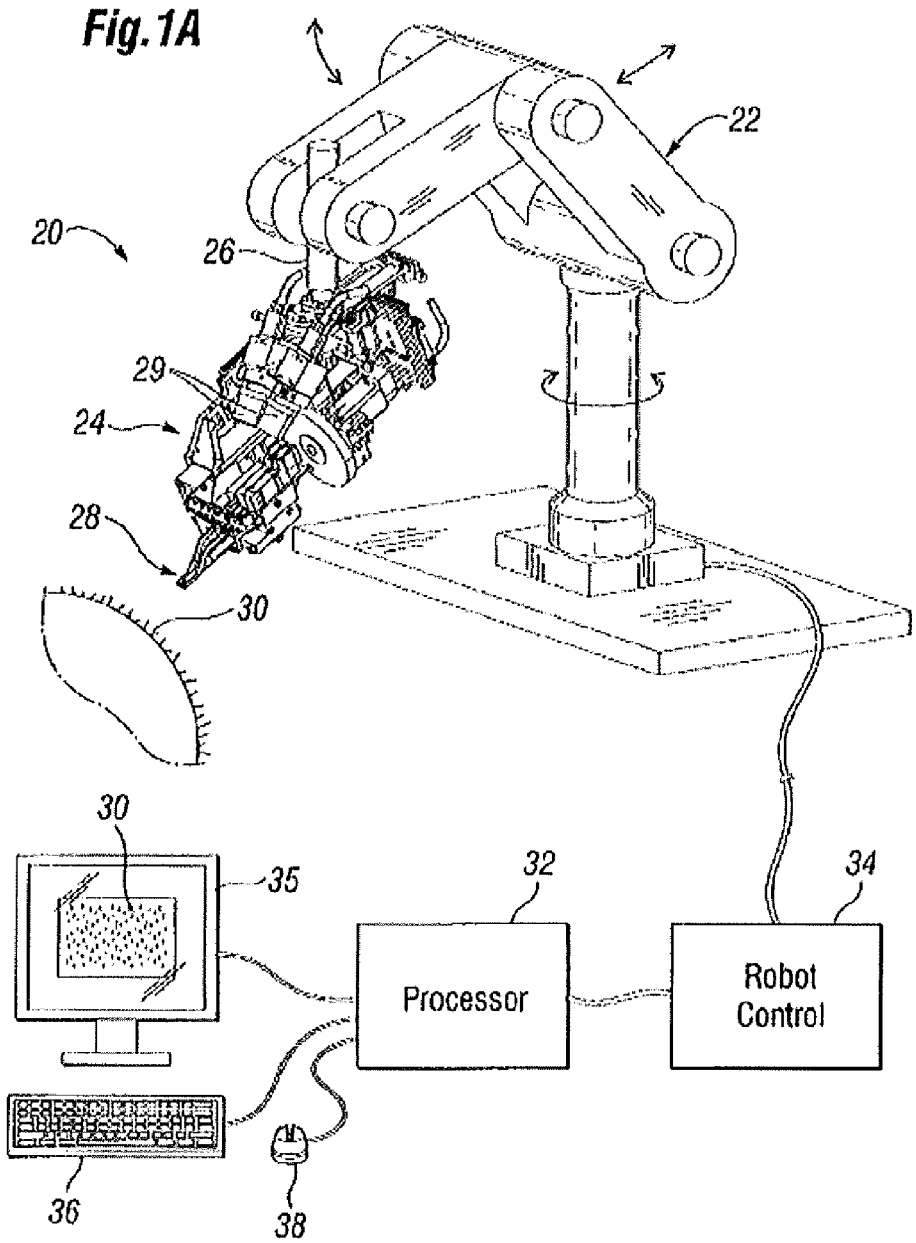
FIG. 1A is a schematic perspective view of an example of a robotic system 20 for hair transplantation that may implement the methodology of the present application.

In the following Detailed Description, reference is made to the accompanying drawings that show by way of illustration some examples of embodiments in which the invention may be practiced. In this regard, directional terminology, such as "right", "left", "upwards", "downwards", "vertical", "horizontal" etc., are used with reference to the orientation of the Figure(s) being described. Because components or embodiments of the present application can be positioned or operated in a number of different orientations, the directional terminology is used for purposes of illustration and is in no way limiting. It is to be understood that other embodiments may be utilized and structural or logical changes may be made without departing from the scope of the present disclosure. The following description, therefore, is not to be taken in a limiting sense, but rather provided so that this disclosure will be thorough and complete and will fully convey the scope of the invention to those skilled in the art.

As used herein, the terms hair, hairs and hair follicle(s) are interchangeable, and the term hair graft may refer to a single hair follicle (or F1, which is a follicular unit comprising one hair) or to a follicular unit (FU) comprising multiple (i.e., a plurality of) hair follicles or hairs. The term "tool", as used herein refers to any number of tools or end effectors that are capable of performing an action, procedure or operation in various medical procedures or applications. For example, the tool may be a needle, a dermal punch, surgical scalpel, blades, various types of forceps, surgical instruments, cannula, drills or lasers. With reference to hair transplantation procedures, a "tool" may comprise, for example, a "harvesting tool" capable of dissecting or harvesting follicular units from a skin or body surface, for example, a scalp. Such tools may have many different forms and configurations. In many embodiments, the tool comprises a hollow tubular shaft and thus may be labeled, for example, a cannula, a needle, or a punch. The distal end of such tools (for example, punches, coring devices, cutting and/or trimming devices, needles), are typically sharpened, to various degrees, to penetrate tissue. The terms "operatively connected," "coupled," or "mounted," or "attached" as used herein, means directly or indirectly coupled, attached, or mounted through one or more intervening components.

As further described below in more detail, general embodiment of the present invention determines hair tail positions accurately based on images captured from a body surface without extensive image processing by refining coarse FU image signals associated with target/selected hairs. Intensity information associated with FU image signals are processed for determining rough hair boundaries and orientation axes. Corresponding hair image intensity profiles between intersection points of orientation axes and boundaries are used for determining fine hair tail positions.

The present invention encompasses utilizing various techniques for imaging low-contrast features and structures in order to determine the size, shape, position, and orientation of those low-contrast features and structures, such as moles, hair tails and hair heads. It should be understood that although the methods described herein are especially suited for use with image-guided computer-implemented (e.g. robotic) system, such as robotic systems for hair harvesting, and for convenience of the description the embodiments will be described in reference to hair transplantation, including hair harvesting, the system and methods of the present application can be applied to other automated and/or computer-implemented applications. For example, devices, systems and methods described herein may be utilized in various dermatological procedures. The systems and methods described herein will also provide great benefit to a physician who removes follicular units using a manual FUE technique or with partially/fully automated handheld tools, as it will guide the physician in more accurately positioning such tools to avoid transecting or otherwise damaging the follicular units to be harvested.

Various terms for imaging devices and systems are used herein. The terms imaging device and image sensor are synonymous, and the term camera is also considered to be an image sensor. Image sensors generate, receive and/or sense visible and non-visible images, such as within the visible spectrum, the infrared spectrum or ultrasonic waves. One example of the imaging device is one or more cameras, such as any commercially available cameras. Instead of a camera, it could be a video recording device (such as a camcorder) or any other imaging device.

The system of the present invention incorporates an image processor or processing unit. The image processor may comprise any device programmed and configured to perform the methods according to the present invention. One non-limiting example of a suitable image processor is any type of personal computer ("PC"). Alternatively, the image processor may comprise an Application Specific Integrated Circuit (ASIC) or Field Programmable Gate Array (FPGA). As further described below in connection with FIG. 8, the image processor may be programmed with software configured to implement the present invention. The image processor may comprise one or more modules for executing operations and one or more modules may comprise instructions for performing various steps according to the present invention. For example, one or more modules may contain instructions for determining position of a hair tail according to the present invention. The same or different one or more modules may contain instructions controlling movement of a tool (e.g. dissecting tool, or harvesting tool) relative to the position of the hair tail.

FIG. 1A is a schematic perspective view of an example of a robotic system 20, for example, for follicular harvesting that implements methodology of the present disclosure. The system 20 includes a robotic arm 22 having a head assembly 24 mounted for rotation on a down tube 26 of the robotic arm. Various arrows are shown to illustrate the movement capabilities of the system 20. Furthermore, as will be seen below, motors and other such movement devices incorporated in the head assembly 24 enable fine movements of an operating tip of a tool 28 in multiple directions. The robotic system 20 further includes at least one imaging sensor 29 with imaging capabilities for providing images used for determining hair tail positions according to the present invention.

The operating tip of the tool 28 is shown positioned over a body surface 30, in this case a part of the patient scalp having hair follicles thereon. In reference to hair harvesting system of FIG. 1A, the tool 28 may be any number of harvesting or dissecting tools useful for removing follicular units from the body surface 30. A processor 32 acting, for example, through a robotic control 34 instructs the various movement devices of the robotic arm 22 and head assembly 24. The processor 32 may incorporate in some embodiments an image processor. As an example, the processor 32 may be any type of personal computer. Alternatively, the processor 32 may comprise ASIC or FPGA, or any other appropriate device. An operator monitors conditions and provides instructions through a monitor 35, keyboard 36, and mouse 38. A magnified image of the body surface 30 can be seen on the monitor 35.

Figure 1C:
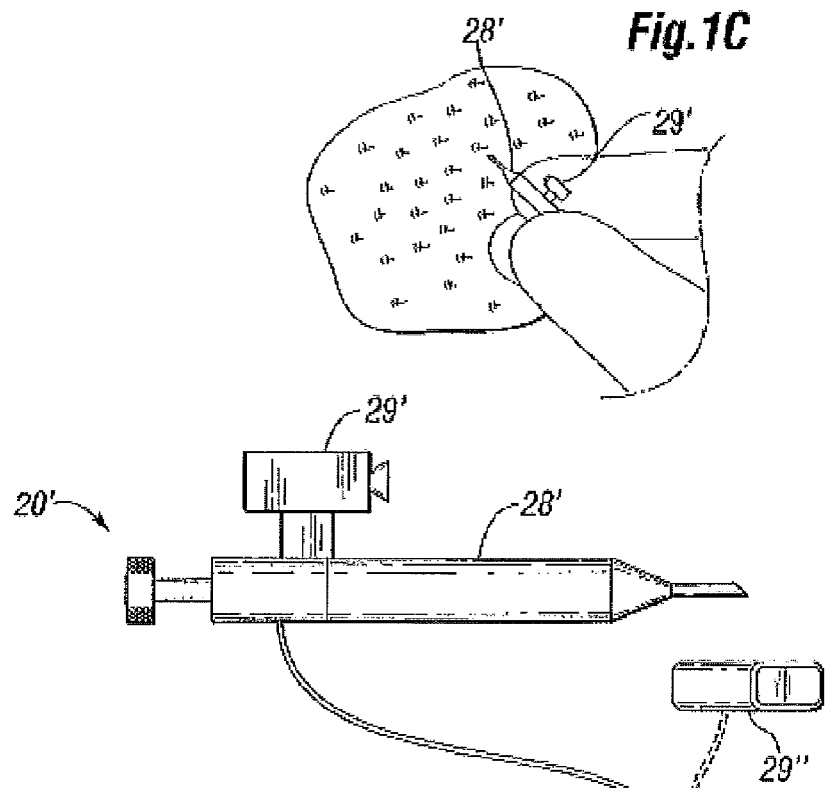
FIGS. 1B and 1C show an alternative system for follicular unit harvesting that may implement methodology of determining hair tail positions according to the present disclosure.
Figure 1B:
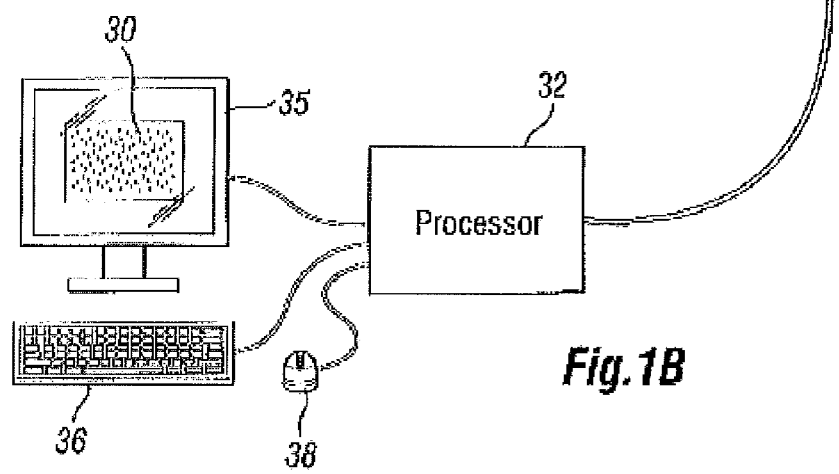

FIGS. 1B and 1C show an alternative system for follicular unit harvesting using hair tail positions determined according to the present invention. Instead of a robotically- or automatically-controlled tool, the user may manipulate a handheld removal tool 28' to remove follicular units based on the determined hair tail positions An imaging sensor 29', such as an infrared camera, may be mounted on the tool and provides real-time images to a processor 32 which generates images to a monitor 35. The surgeon can adjust the angle and position of the tool 28' based on the determined hair tail positions. Alternatively, an optional ultrasound sensor 29" may be used, which is also shown attached to the system 20'. The ultrasound sensor 29" may be used prior to the harvesting or removal step to map the surface (and subsurface) configurations of select follicular units, which information can then be referenced and shown on the monitor 35. The monitor may provide notification to the user that the tool as positioned may transect the hair if maintained at the angle at which the user is currently holding it. The system may, alternatively, notify the user that operating the tool at the current angle will be unlikely to transect the hair. In this arrangement, the imaging sensor 29' may be a standard visible light camera, or stereo cameras.

The image data is acquired by the imaging device or sensor, such as imaging device 29, and processed by the processor to identify objects of interest, such as hair, in the camera frame. From images of a region of interest on the body surface, software residing, for example, in the computer performs methodology of determining hair tail position on a body surface according to the present disclosure.

The system, such as the system 20, may identify a position and orientation of a selected hair relative to a donor area, for example, a scalp, including the angle from the scalp, so that the harvesting tool may be positioned accordingly relative to the orientation of the hair and relative to the hair tail position.

Complete hair tail position information according to the present application may be determined up front, for example, in case of the manual hair transplantation procedure. In the automated, including robotic implementation, hair tail position information may be used to move position or operate a tool for performing procedure. In yet another embodiment, hair tail position information could be determined on the go, or in real-time, as the tool moves.

Figure 2B:
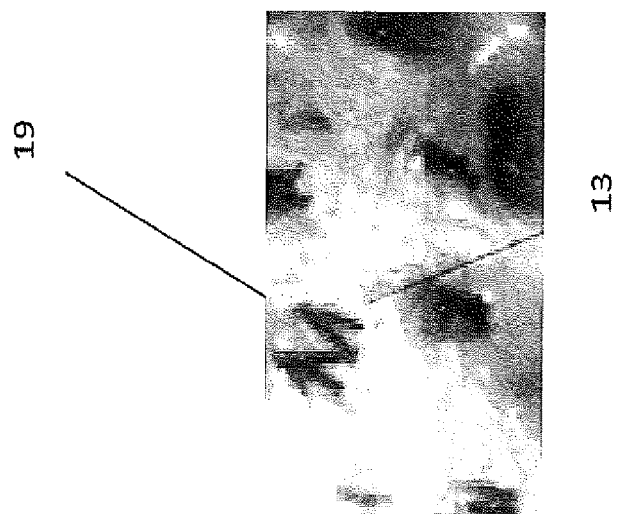
FIGS. 2A and 2B show an image of a body surface received from an imaging device.
Figure 2A:
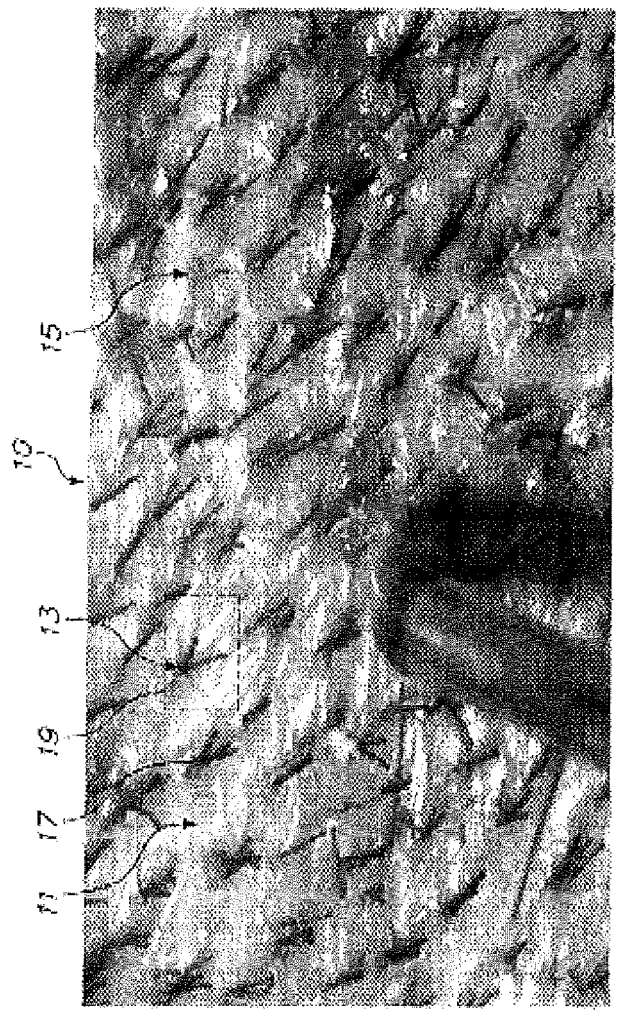

FIG. 2A shows an image 10 of a body surface 11 received from an image acquisition or imaging device. By way of example, the digital image 10 shows hair in a variety of arrangements of follicular units (FU) on the scalp 11, including a single follicle (F1) follicular unit 15, a two follicle (F2) follicular unit 13, and a three follicle (F3) follicular unit 17. FIG. 2B shows a region of interest 19, which is known to contain a target FU 13. The region of interest 19 may be selected by an operator or the selection may be made automatically by the system.

Figure 4:
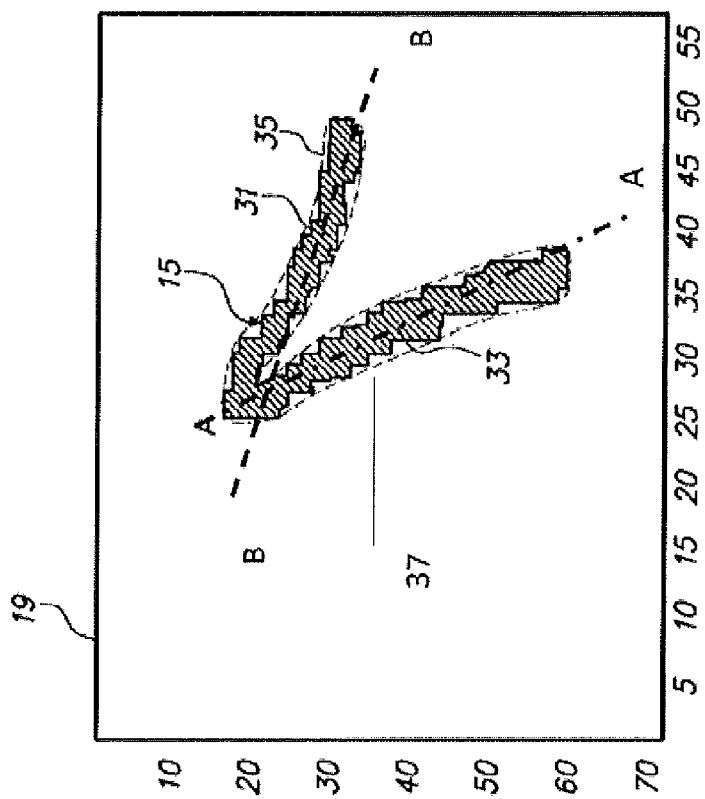
FIG. 4 shows by example the hair graft of FIG. 3 after segmentation, and showing a contour of the graft and each hair follicle of the hair graft.
Figure 3:
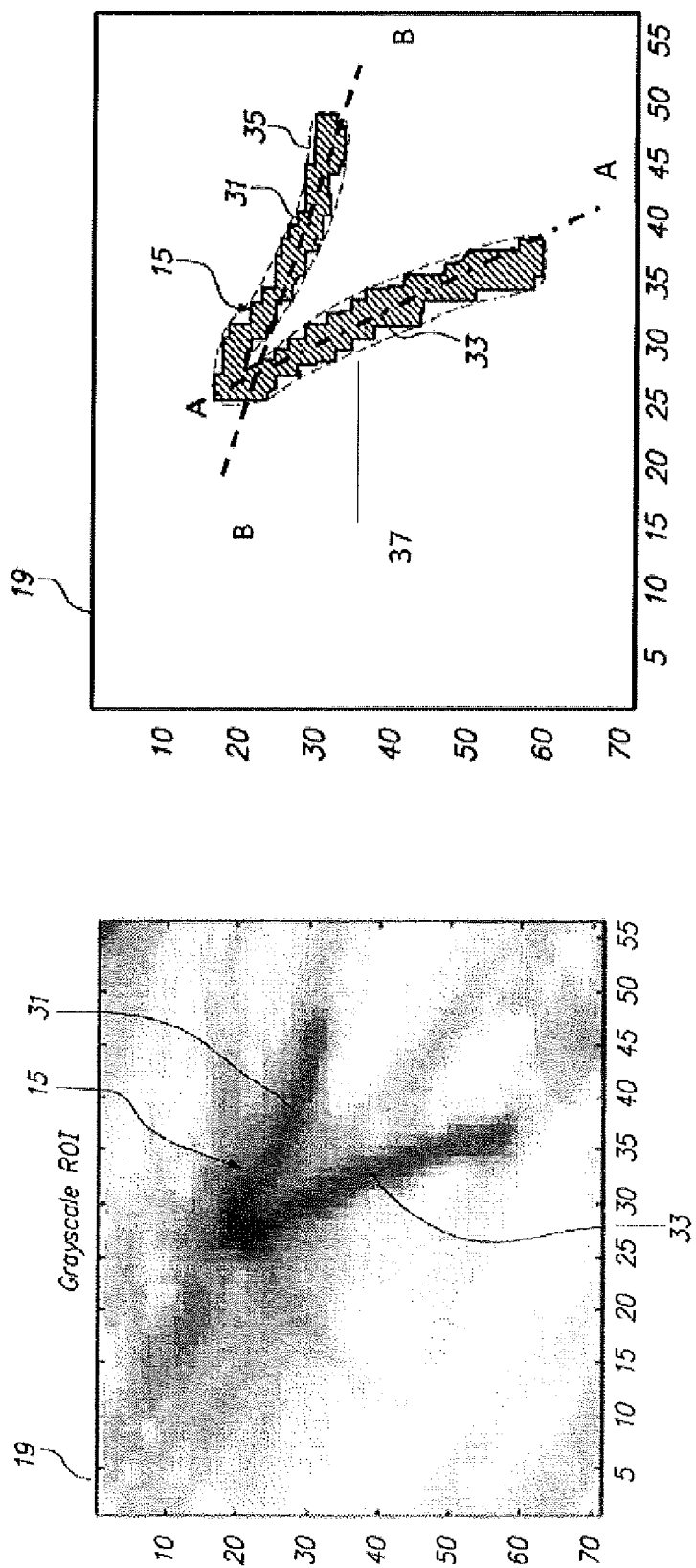
FIG. 3 shows a magnified row image of a hair graft within a region of interest.

FIG. 3 shows an example of a grayscale region of interest 19 with a magnified image of follicular unit FU 15, which includes two (2) hair follicles 31 and 33. The grayscale image may be segmented, as shown in FIG. 4. Image segmentation partitions the image into multiple segments known as sets of pixels. Segmentation simplifies the images within the region of interest 19 for locating objects and boundaries (lines, curves, etc.). Image segmentation assigns a label to every pixel in the image such that pixels with the same label share certain visual characteristics.

FIG. 4 shows segmented image of hairs 31 and 33 of FU 15, including a rough generated contour. Due to the glare of the lighting, shadow from the instrument, transparent skin nature, and noisy image quality, often, the hair object may be over segmented, and the contour may appear larger than the real one. Any known contour tracking algorithm or method may be used to generate, for example, a rough contour that defines rough boundaries for the follicular unit and for the individual hair follicles of FU 15. One exemplary tracking algorithm is disclosed in S. Suzuki and K. Abe, "Topological structural analysis of digital binary images by border following," Computer Vision, Graphics and Image Processing 30 (1985):32-46. In some embodiments, an extra step may be required to separate the two longitudinal axes of each hair follicle of the follicular unit.

FIG. 4 shows the outer perimeter of the follicles 31 and 33 of the binary image defining a "V" shaped contour of a two-follicle follicular unit 15 (shown in dotted line). As shown in FIG. 4, the "V" shape of FU 15 is formed along two intersecting longitudinal axes A-A and B-B. The A-A axis, associated with hair 33, runs along a contour 37 of the hair 33 and the B-B axis associated with hair 31 runs along a contour 35 of the hair 31. While the FU 15 is of type F2, it would be appreciated that the details of the invention describe below are equally applicable to any type of FU, including F1 and F3-F5. The methods of the present application determine a longitudinal or major axis corresponding to the direction or orientation of each of the hair 31 and 33 of the follicular unit or hair graft 15. Image moments of the contour, as well as information pertaining to the centroid of the contour (or center of region bound by the contour), may be used to provide direction and orientation of the longitudinal axes A-A and B-B. For example, the 0 order moment of the contour may provide information on position of the longitudinal axis of each hair follicle and the $1^{st}$ order moment of the contour may provide information as to the direction.

In some embodiments it may not be necessary to determine the contour and contour moments of each hair follicle in a follicular unit. For example, if two hair follicles of the follicular unit exit the body surface through a common point, or exit the body surface at a distance less than a predetermined distance from each other, then the contour, the major axis and the refined hair tail may be determined just for one of these closely positioned hair follicles. The refined hair tail located for one hair follicle may be applied to both hair follicles of the above-mentioned follicular unit. In another embodiment, similar methodology may be applied to hair grafts that have at least two hairs that are located close together and oriented with a small angle (for example, less than 30°) between them, or have at least two hairs closely located substantially parallel to each other. In yet another alternative implementation, the refined hair tail of one hair follicle may be determined and the others disregarded. In a further alternative embodiment, the contour and the contour moments for each hair follicle may be determined, and the refined hair tail determined for each hair follicle. The results of these determinations may be compared to further confirm the refined locations of the hair tails. In some implementations, rather than utilizing the information regarding the refined hair tail from each individual hair follicle, the results may be averaged, and the average hair tail location utilized when directing and positioning the tool. The above-described and other variations are all within the scope of the present application. The following description provides an example of methodology of determining and refining a hair tail according to the present application in reference to an individual hair follicle or a follicular unit comprising one hair follicle. However, it will be understood that the description below may be adjusted for determining hair tails of the hair grafts containing multiple follicular units based on various principles, examples of which are listed above.

Figure 5:
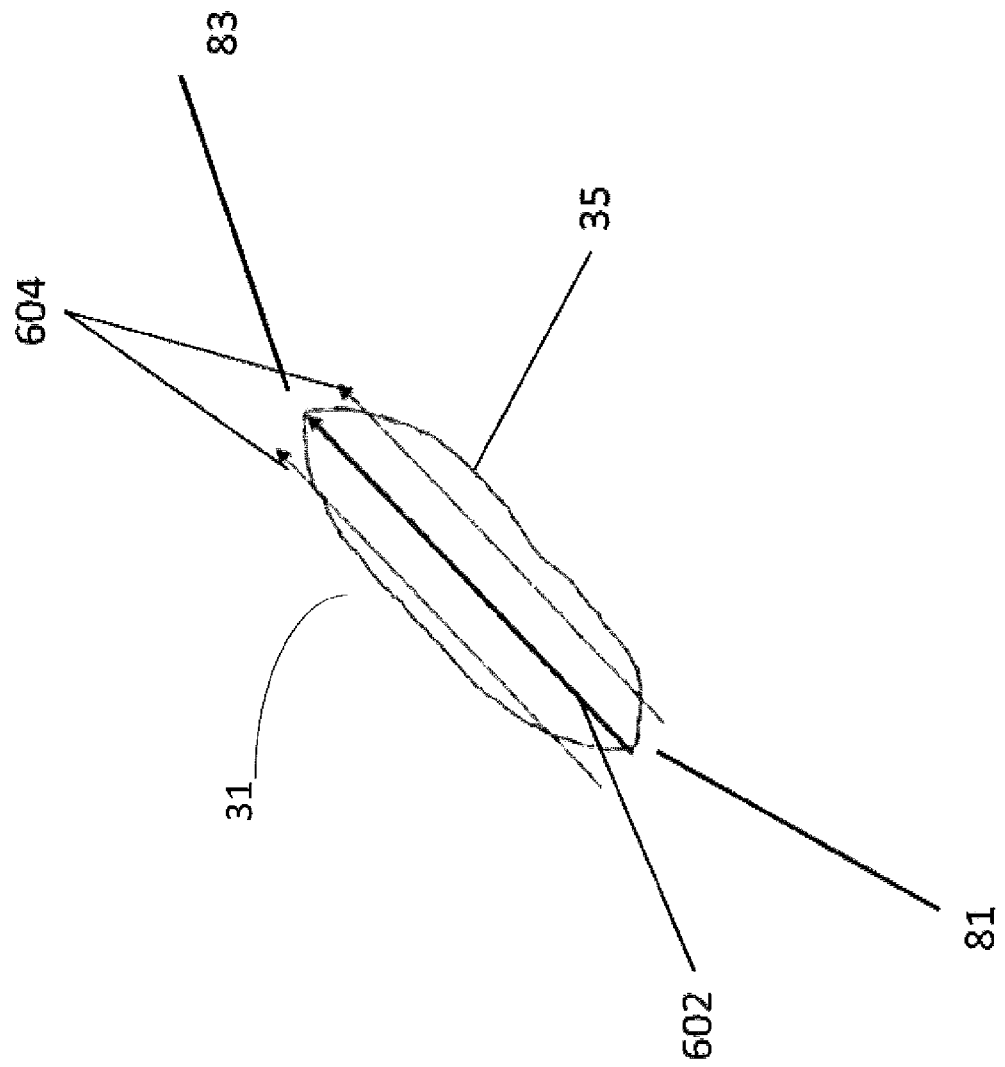
FIG. 5 shows an example of the contour of a hair follicle with a longitudinal or major axis of the hair follicle intersecting the contour.

With reference to hair follicle, for example a hair follicle 31 of FIG. 4, FIG. 5 demonstrates how the end points of the hair 31 and parallel intensity profile of the hair 31 may be generated. A longitudinal axis (or a major axis) for hair 31 is shown as 602. It may be determined using a first order moment calculation of contour 35. Results obtained from the first order moment calculation provide the direction of the longitudinal axis 602 expressed in terms of an orientation angle, for example. The center of the region bound by the contour provides a point within the contour, which the longitudinal axis 602 will go through. An intensity profile for the hair 31 may be generated by processing/recording image intensity values along the longitudinal axis 602. Optionally, intensity values along several additional axes 604 which are generally substantially parallel to the major longitudinal axes 602 can be used for a more robust intensity profile generation. FIG. 5 shows parallel intensity profiles along axes 604 from several neighboring pixels parallel to pixels associated with the longitudinal axis 602 within contour 35. For example, parallel intensity profiles within 2-5 pixels on either side of the longitudinal axis 602 may be determined. As can be seen in FIG. 5, the longitudinal axis 602 of hair 31 and the contour 35 intersect with each other at two opposing end points 81 and 83. The intersection point 81 is associated with a coarse hair tail position for the hair 31 and the intersection point 83 is associated with the hair head position for hair 31. As such, under one embodiment of the present invention, the intersected points between hair axis and rough contour are calculated, and then classified as the tail and the head positions of the hair.

Figure 6:
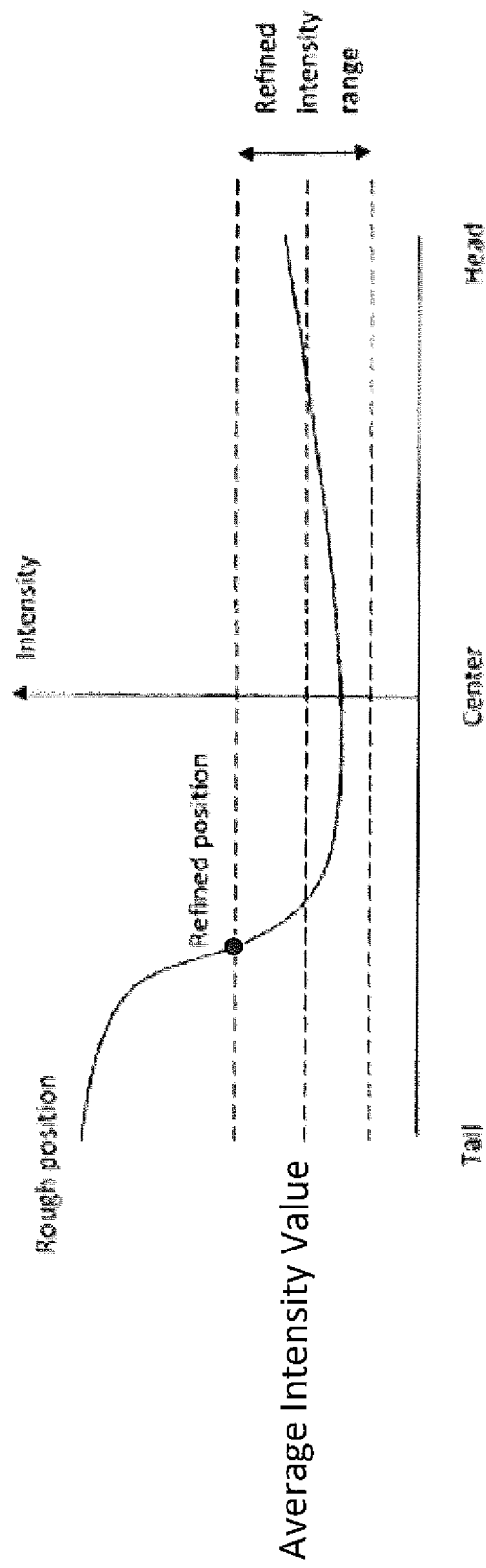
FIG. 6 shows an example of an intensity profile associated with the hair between the intersecting points of FIG. 8.

FIG. 6 shows one example of the generation of the refined hair tail. The intensity profile of hair 31 between the coarse/rough hair tail position 81 and hair head position 83 is demonstrated. The coarse position of the hair tail of the hair 31 may be refined based on calculation of the intensity levels, as well as statistics or statistical information associated with the intensity profile. In one embodiment, such refinement is based on calculation of an average intensity level derived from the intensity profile. More specifically, the central region of the intensity profile shown in FIG. 6 is used to calculate an averaged intensity. It is assumed that this intensity level is close to the true natural intensity of the hair 31. Statistical information associated with the hair image intensity profile, which may comprise a standard deviation of the intensity value along the hair from the average intensity value may be determined. Under one arrangement, a number of standard deviations measured from the center of the longitudinal axis of the hair relative to the coarse tail position is used to refine the coarse hair tail position. For example, the standard deviation of the profile based on the average intensity value is calculated. In one example, the average intensity value plus/minus two times of the standard deviation from the center position is used as the basis for refining the coarse position. As shown in FIG. 6, the end point, truncated at twice the standard deviation along the longitudinal axis, may be selected as the refined hair tail position for hair 31. Other statistical approaches for refinement include averaging determined tail positions from image information from multiple cameras. Further, in some embodiments smoothing of the tail position based on historical data can be used to reduce the noise caused by image quality. Under this arrangement, the hair tail refinement results in each frame may be buffered and compared using a smoothing filter (shown in FIG. 8).

Accordingly, statistical information associated with the intensity profile of the image may comprise a standard deviation determined based on an average intensity level derived from averaged intensities within a central region of the intensity profile. The refined position of the hair tail may be determined based on a number of standard deviations measured from a center of the longitudinal axis of the hair relative to the coarse position of the hair.

Figure 7:
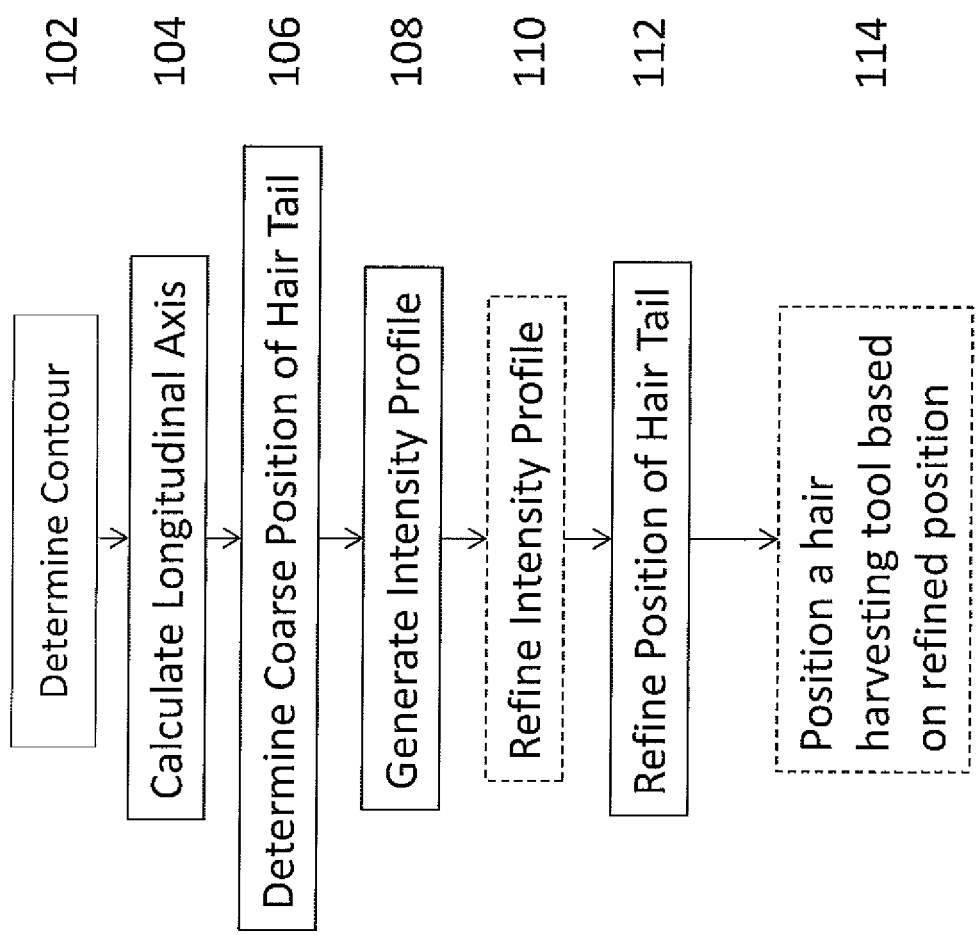
FIG. 7 shows a flow chart of an example of a method according to the present application.

FIG. 7 shows the flow chart of one example of a method that may be implemented with the present disclosure, for example, a method for determining a refined position of a hair tail of at least one hair of a hair graft (the hair graft may contain only one hair, or it may be a multiple hair follicular unit) and, optionally, improving position of a tool relative to the hair graft. The method shown in FIG. 7 determines a contour of a hair from an image of a body surface, for example, taken by an imaging device, block 102. A longitudinal axis corresponding to orientation or direction of the hair is determined/calculated, block 104. I Intersection points of the longitudinal axis of the hair and contour of the hair are determined. One of the intersection points is associated with a coarse position of a hair tail of the hair on the body surface, block 106. The method further comprises generating an intensity profile of the image of the hair, for example, along the longitudinal axis of the hair, 108, followed by refining the coarse position of the hair tail based on the intensity profile of the image, block 112. Optionally, the intensity profile itself may be subject to refinement, block 110. Such optional intensity profile refinement may comprise calculating average intensity profile and intensity statistics. In certain implementations, the method may further comprise an optional step of positioning a tool, for example, a hair harvesting tool, relative to the hair based on the refined position of the hair tail, block 116.

Figure 8:
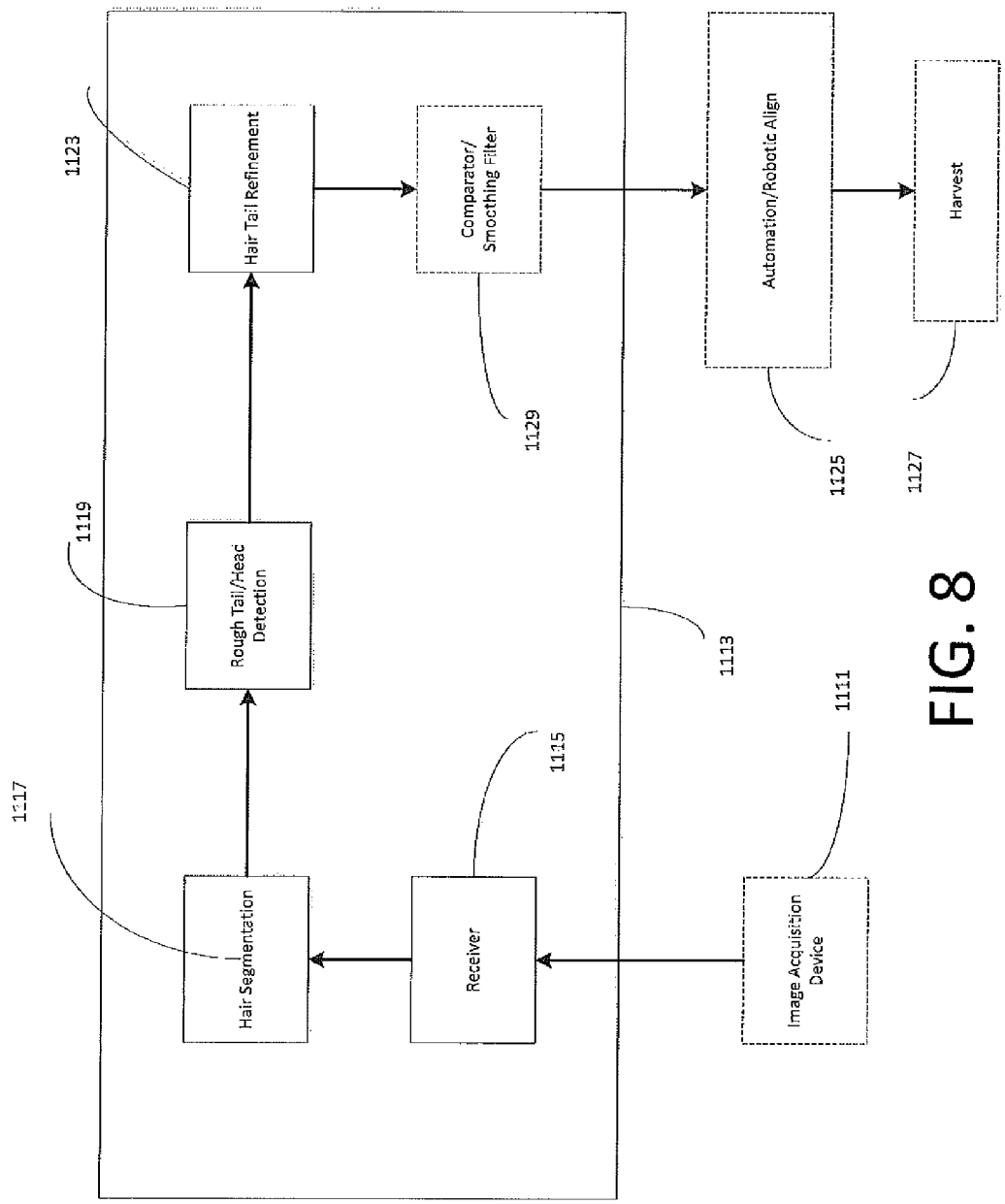
FIG. 8 shows a block diagram of an example of a system for determining a position of a hair tail and, optionally, performing a procedure, such as hair harvesting.

FIG. 8 shows a block diagram of an example of a system for determining a position of a hair tail on a body surface. The system includes an image processor/unit 1113 configured to receive image signal via a receiver 1115. The processor 1113 executes instructions for processing image signal received from an imaging device. The imaging device, in some embodiments, may be included in the system. The processor (or image processor) may comprise one or more modules for performing various instructions according to the methodology described in the present application. For example, it may comprise a hair segmentation module 1117 which may segment the image and provide a rough contour for a target hair. A detection module 1119 may detect rough/coarse head and tail positions at the intersection points of the rough contour along a longitudinal axis. A hair refinement module 1123 may generate intensity profile of the image of between the hair coarse head and tail positions and optionally refine the coarse position of the hair tail. Optionally, is some embodiments, an automation/robotic module 1125 may direct movement of a robotic arm to position a tool (e.g., harvesting tool) relative to the hair. Of course, the robotic arm may be controlled by a different processor. In one embodiment, the imaging device may be located on the robotic or movable arm. The robotic arm may be positioned based on the refined position of the hair tail. Another optional module may control operation of the tool, for example, to harvest hair graft.

As such, an image processing unit according to the present invention comprises a receiver configured to receive an image of a hair on a body surface and a processor coupled to the receiver. As stated above, the processor is configured to refine a coarse position of a hair tail found within the image along a longitudinal axis of the hair that is derived from an intensity profile of the image. In order to further improve the refining process, hair tail positions derived from a plurality of imaging devices may be averaged in various methods described in reference to various embodiments. Also, refined positions from a plurality of sequentially taken images can be compared, for example, by a smoothing filter 1129 which is shown in dotted line as an optional feature in FIG. 8.

Figure 9B:
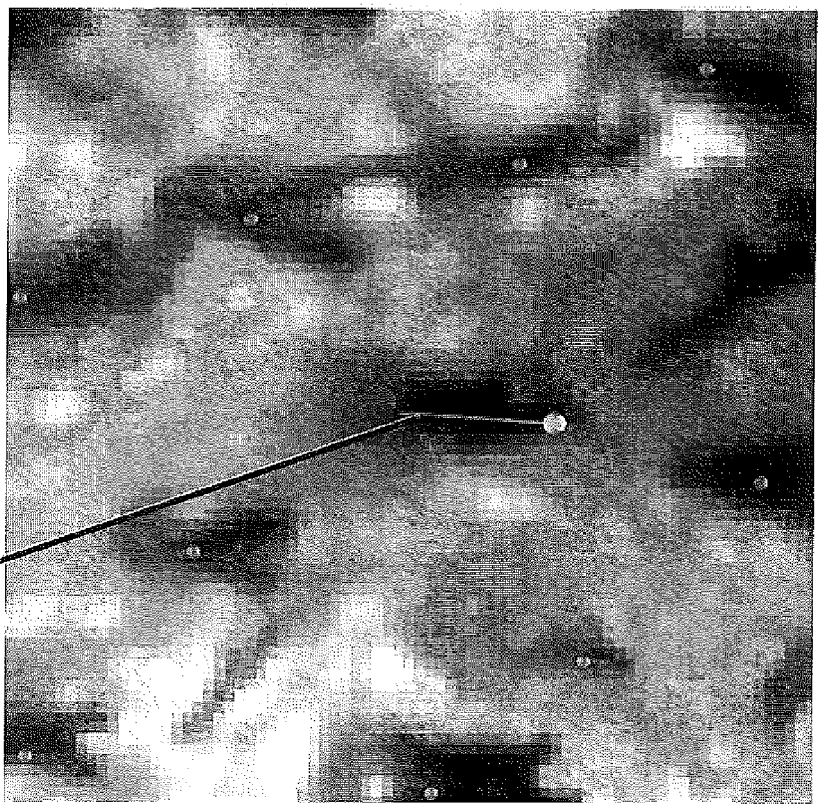
FIG. 9B depicts a refined hair tail position after application of the methodology of the present disclosure.
Figure 9A:
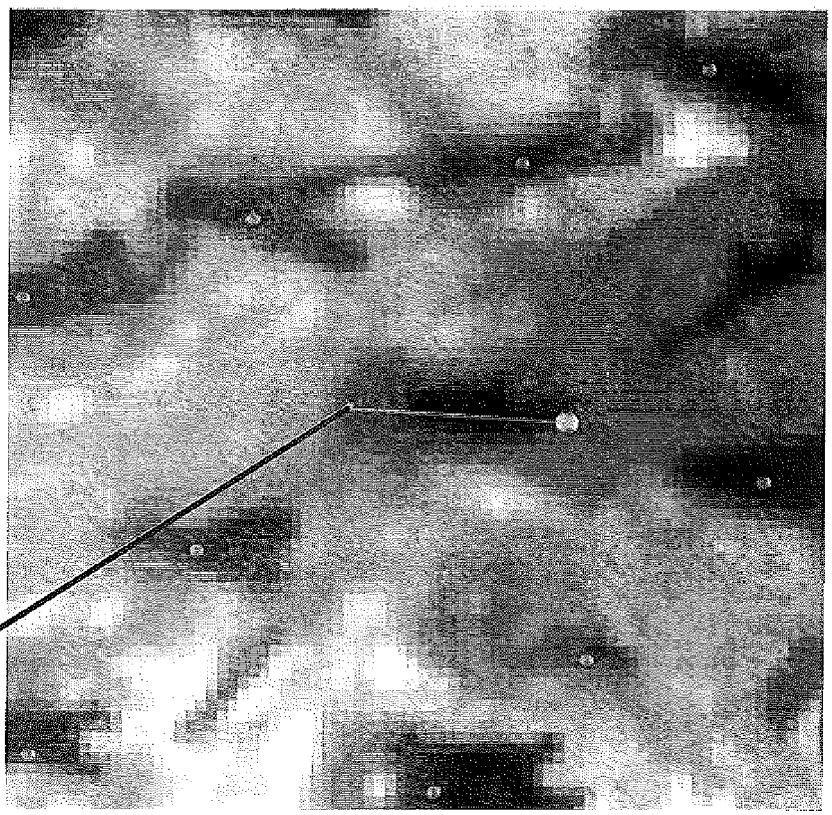
FIG. 9A demonstrates an original coarse hair tail position.

FIG. 9A shows an image with a coarse hair tail position 92 of a hair before application of the methods as described herein. FIG. 9B shows the refined hair tail position 94 of the same hair after application of the methods of the present application. As could be seen in FIG. 9B, the refined hair tail position 94 determined according to the present invention provides a more accurate position compared to the coarse hair tail position 92 shown in FIG. 9A. This accuracy allows for better positioning of automated tools in a variety of hair transplantation applications, including positioning of the harvesting tool 28 shown in FIG. 1A. Similarly, tool 28' shown in FIGS. 1B and 1C could be more accurately positioned in manual hair transplantation applications.

The various embodiments described above are provided by way of illustration only and should not be construed to limit the claimed invention. These embodiments are susceptible to various modifications and alternative forms, and it should be understood that the invention generally, as well as the specific embodiments described herein, cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment.

Further, those skilled in the art will recognize that the devices, systems, and methods disclosed herein are not limited to one field, such as hair restoration, but may be applied to any number of fields. The description, therefore, is not to be taken in a limiting sense, and the scope of the present invention is defined by the appended claims. It will be further appreciated by those skilled in the art that the invention is not limited to the use of a particular system, and that automated (including robotic), semi-automated, and manual systems and apparatus may be used for positioning and actuating the respective removal tools and other devices and components disclosed herein.

The invention claimed is:

1. A method for determining a position of a hair tail on a body surface, comprising:
    using a processor to perform one or more of the following steps:
    determining a contour of a hair from an image of a body surface taken by an imaging device;
    determining a longitudinal axis of the hair;
    determining intersection points of the longitudinal axis of the hair and the contour of the hair, wherein one of the intersection points is associated with a coarse position of a hair tail of the hair on the body surface;
    generating an intensity profile of an image of the hair along the longitudinal axis of the hair; and
    refining the coarse position of the hair tail based on at least the intensity profile of the image.

2. The method of claim 1, wherein generating the intensity profile of the image comprises using statistical information.

3. The method of claim 2, wherein the longitudinal axis of the hair is derived from a first order moment of the contour.

4. The method of claim 1, further comprising smoothing the refined coarse position of the hair tail to reduce noise.

5. The method of claim 4, further determining the intensity profile along one or more orientation axis that is substantially parallel to the longitudinal axis of the hair.

6. The method of claim 2, wherein said statistical information associated with the intensity profile of the image of the hair comprises a standard deviation determined based on an average intensity level derived from averaged intensities within a central region of the intensity profile.

7. The method of claim 6, wherein refining the coarse position of the hair tail is done using a number of standard deviations measured from a center of the longitudinal axis of the hair relative to the coarse tail position.

8. The method of claim 1, further comprising averaging refined positions of the hair tail derived from a plurality of images of the body surface.

9. The method of claim 1, further comprising comparing refined positions of the hair tail derived from a plurality of sequentially taken images of the body surface.

10. The method of claim 9, wherein said refined hair tail positions are compared by smooth filtering.

11. The method of claim 1, wherein the contour of a hair is determined by using a segmentation of the image of the body surface.

12. The method of claim 1, wherein the hair is associated with a follicular unit comprising a plurality of hairs, the method further comprising refining coarse positions of hair tails associated with each one of the plurality of hairs of the follicular unit.

13. The method of claim 1, wherein the hair is associated with a follicular unit comprising a plurality of hairs that exit the body surface through a common point, and wherein the refined hair tail position of the hair is applied to the rest of the plurality of hairs that exit the body surface through the common point if the hair is among the plurality of hairs that exit the body surface through the common point.

14. The method of claim 1, wherein the hair is associated with a follicular unit comprising a plurality of hairs that exit the body surface at a distance that is less than a predetermined distance from each other, and wherein the refined hair tail position of the hair is applied to the rest of the plurality of hairs that exit the body surface at the distance that is less than the predetermined distance from each other if the hair is among the plurality of hairs that exit the body surface at the distance that is less that the predetermined distance from another one of the plurality.

15. The method of claim 1, wherein the hair is associated with a follicular unit comprising a plurality of hairs that exit the body surface at an angle that is less than a predetermined angle, and wherein the refined hair tail position of the hair is applied to the rest of the plurality of hairs that exit the body surface at the angle that is less than the predetermined angle if the hair is among the plurality of hairs that exit the body surface at the angle that is less than the predetermined angle.

16. A method for improving position of a hair harvesting tool relative to a hair graft to be harvested, comprising:
    determining a contour of a hair of a hair graft from an image of a body surface taken by an imaging device;
    determining a longitudinal axis of the hair;
    determining intersection points of said longitudinal axis of the hair and said contour of the hair, wherein one of the intersection points is associated with a coarse position of a hair tail of the hair on the body surface;
    generating an intensity profile of an image of the hair along the longitudinal axis of the hair;
    refining the coarse position of the hair tail based on at least the intensity profile of the image of the hair; and
    positioning a hair harvesting tool relative to the hair graft based on the refined position of the hair tail of the hair of the hair graft.

17. The method of claim 16, further comprising harvesting the hair graft with the hair harvesting tool.

18. The method of claim 16, wherein the hair graft comprises a plurality of hairs, the method comprising refining coarse positions of hair tails associated with each one of the plurality of hairs of the hair graft.

19. The method of claim 16, wherein the longitudinal axis of the hair is derived from a first order moment of the contour.

20. The method of claim 16, wherein the refined position of the hair tail is determined based on statistical information associated with the intensity profile of the image of the hair.

21. The method of claim 20, wherein said statistical information associated with the intensity profile of the image comprises a standard deviation determined based on an average intensity level derived from averaged intensities within a central region of the intensity profile, and wherein said refined position of the hair tail is determined based on a number of standard deviations measured from a central part of the longitudinal axis of the hair relative to the coarse position of the hair tail.

22. A system for determining a position of a hair tail on a body surface, comprising:
    a receiver configured to receive an image of a hair on a body surface; and
    a processor configured to execute instructions for:
    refining a coarse position of a hair tail of the hair, wherein the coarse position is refined based on at least an intensity profile of the image of the hair.

23. The system of claim 22, further comprising a robotic arm and a harvesting tool operably attached to the robotic arm.

24. The system of claim 23, further comprising an imaging device located on the robotic arm.

25. The system of claim 22, wherein the processor is configured to execute instructions for positioning a harvesting tool relative to the hair based on the refined hair tail position.

26. The system of claim 22, wherein the image processing unit is configured to determine the coarse position of the hair tail by intersecting a hair contour with a longitudinal axis of the hair.

27. The system of claim 22, wherein the processor is configured to generate the intensity profile of the image using statistical information, the statistical information comprising a standard deviation based on an average intensity level derived from averaged intensities within a central region of the intensity profile.

28. The system of claim 22, wherein the receiver is configured to receive a plurality of images of the body surface, and wherein the processor is configured to execute instructions for refining the coarse position of the hair tail by averaging refined positions of the hair tail derived from the plurality of images.

29. An image processor comprising one or more modules for executing operations on images, the one or more modules comprising instructions for:
- determining a contour of a hair from an image of a body surface taken by an imaging device;
- determining a longitudinal axis of the hair;
- determining intersection points of the longitudinal axis of the hair and the contour of the hair, wherein one of the intersection points is associated with a coarse position of a hair tail of the hair on the body surface;
- generating an intensity profile of the image along the longitudinal axis of the hair; and
- refining the coarse position of the hair tail based on at least the intensity profile of the image.

* * * * *